United States Patent [19]
Zenty

[11] 4,306,940
[45] Dec. 22, 1981

[54] APPARATUS FOR VAPOR COMPRESSION FRACTIONAL DISTILLATION OF LIQUID MIXTURES

[75] Inventor: Stephen Zenty, Rockville, Md.
[73] Assignee: Evapro-Tech, Inc., Eau Claire, Wis.
[21] Appl. No.: 148,678
[22] Filed: May 12, 1980
[51] Int. Cl.³ .................. B01D 3/26; C07C 29/80
[52] U.S. Cl. ..................... 202/83; 202/153; 202/179; 202/185 D; 202/234; 202/242; 203/19; 203/25; 203/26; 203/98; 203/DIG. 1; 203/DIG. 8; 203/DIG. 13; 203/DIG. 22
[58] Field of Search ............ 203/DIG. 1, 24, 26, 203/19, 98, DIG. 22, DIG. 13, DIG. 8; 202/180, 179, 153, 161, 270, 198, 185 D, 185 E, 182, 234, 83, 158, 242; 435/161; 426/493, 494

[56] References Cited

U.S. PATENT DOCUMENTS

| | | | |
|---|---|---|---|
| 1,257,470 | 2/1918 | Filippo et al. | 202/158 |
| 2,070,100 | 2/1937 | Twomey | 202/158 |
| 2,456,562 | 12/1948 | Lindsay | 203/DIG. 1 |
| 2,637,684 | 5/1953 | Buffum | 203/24 |
| 3,336,207 | 8/1967 | Peterson | 203/26 |
| 3,349,007 | 10/1967 | Ciborowski et al. | 203/26 |
| 3,351,536 | 11/1967 | Fox | 203/83 |
| 3,382,157 | 5/1968 | Barnstead | 203/DIG. 22 |
| 3,568,457 | 3/1971 | Briggs et al. | 203/26 |
| 3,635,799 | 1/1972 | Lowi | 203/83 |
| 3,801,474 | 4/1974 | Castellucci et al. | 203/DIG. 1 |

FOREIGN PATENT DOCUMENTS

2398023  3/1979  France ............ 203/DIG. 1

Primary Examiner—Wilbur L. Bascomb, Jr.
Attorney, Agent, or Firm—Schwartz, Jeffery, Schwaab, Mack, Blumenthal & Koch

[57] ABSTRACT

A process and apparatus especially suited for distilling alcohol from aqueous fermentation liquors wherein liquid vapors from a body of a liquid mixture (4) which is to be distilled pass from a container (2) holding the liquid mixture to a vapor heating chamber (8) disposed above the container where the vapors are heated by solar radiation and/or heat exchange with a source of process heat. The vapors are then withdrawn from the vapor heating chamber, compressed, passed in heat exchange relation with the liquid mixture and introduced into a reflux column (15) disposed in the interior of the body of liquid to be distilled near the center of the container. An aqueous fraction (24) is collected from the bottom of the reflux column, and an alcohol vapor fraction is withdrawn from the top of the reflux column and further condensed in heat exchange contact with the liquid mixture to produce an alcohol fraction (32). Condensation of the vapors in heat exchange contact with the distilland mixture causes the heat released by the condensation to be recycled to the distilland to promote further evaporation.

20 Claims, 1 Drawing Figure

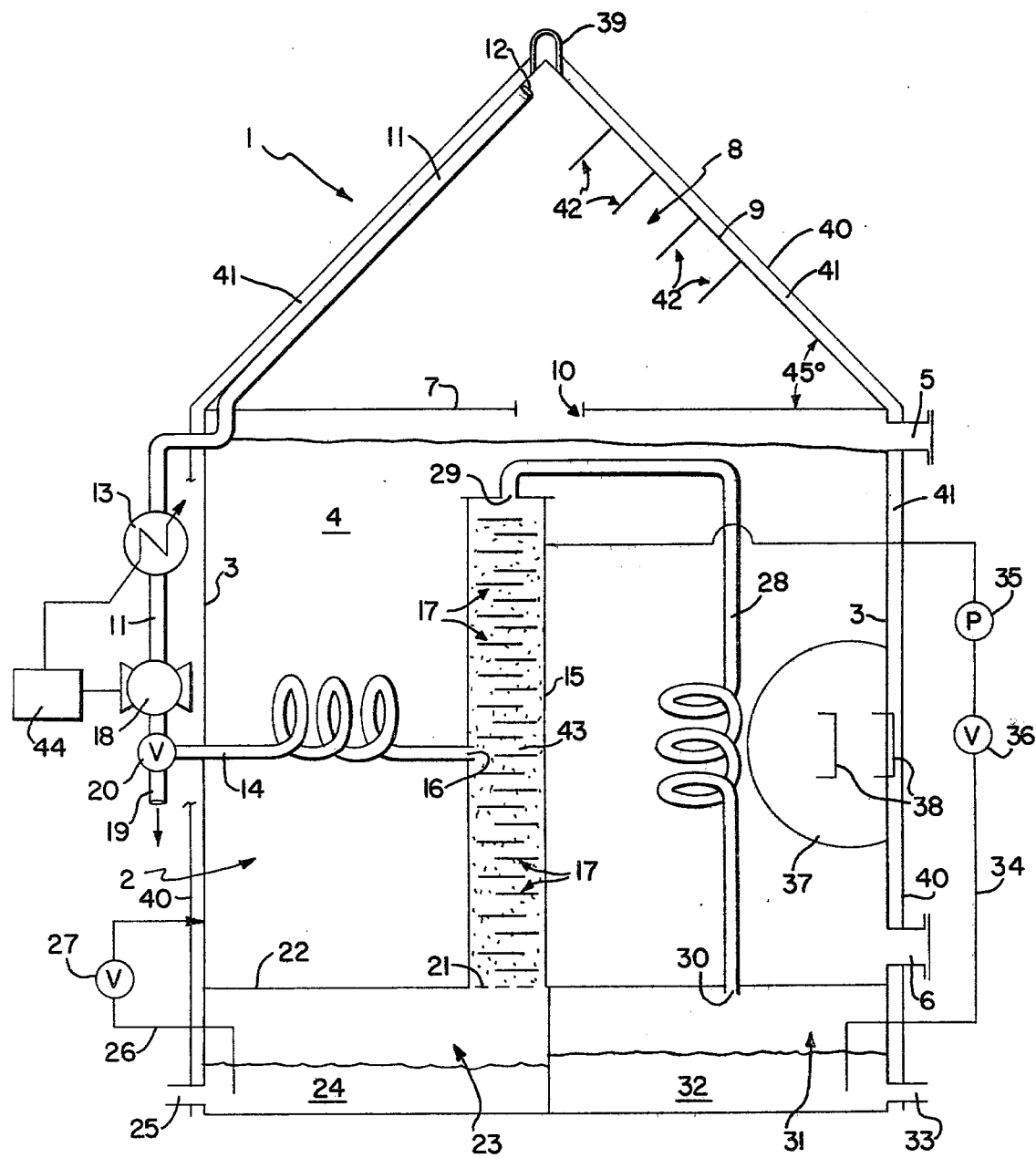

APPARATUS FOR VAPOR COMPRESSION FRACTIONAL DISTILLATION OF LIQUID MIXTURES

BACKGROUND OF THE INVENTION

Disruptions which have occurred in recent years in the supply of petrochemical fuels have brought about an extensive search for alternate fuel sources. Considerable attention has been focused on the use of alcohol produced by biomass fermentation (e.g., fermentation of agricultural wastes) as a substitute fuel. Alcohols make excellent fuels. The constant renewal of biomass sources which can be fermented to produce alcohol could produce massive supplies of fuel in perpetuity. However, biomass fermentation to produce alcohol yields only solutions containing relatively low concentrations of alcohol, usually between about 10 and about 15%. Before the alcohol can be used as a fuel, it must be separated from the remainder of the fermentation liquor.

Separation of such liquid mixtures is an age-old technical problem. Distillation is a well known way of separating and purifying liquids. Traditional distillation methods are, however, relatively inefficient from an energy standpoint. When traditional distillation technologies are utilized to separate the alcohol from a fermentation liquor, disproportionate amounts of energy are consumed. Some workers have reported that when the energy required for cultivation and transportation of the necessary biomass is included with the energy consumed in distilling the alcohol from the fermentation liquor, the total amount of energy consumed may be greater than the energy content of the alcohol produced.

Numerous efforts have been made to develop more efficient distillation processes. Attempts have been made to increase efficiencies by returning part of the heat of condensation of distilled vapors back to the distilland liquid to promote further evaporation (see Harding, et al., U.S. Pat. No. 3,032,481). Distillation systems have also been developed for producing fresh water from seawater which attempt to conserve energy by recovering a portion of the heat of condensation of the distilled liquid (see Mahistre, U.S. Pat. No. 3,494,835). Other workers have attempted to use solar energy to distill liquids such as seawater (see Duffy, U.S. Pat. No. 3,330,740).

Such systems have not proved completely satisfactory. In may cases, large, complex and prohibitively expensive apparatus has been required. In other cases, thermal efficiencies are still too low for effective operation. There remains a real need for a simple, relatively small, functional and highly economical distillation system which can be used to separate alcohol from aqueous fermentation liquors.

OBJECTS OF THE INVENTION

Accordingly, it is an object of the present invention to provide a distillation process and apparatus which is simple, functional and economical to construct and operate.

Another object of the present invention is to provide a distillation process and apparatus with a very high degree of thermal efficiency.

A further object of the present invention is to provide a distillation process and apparatus which effectively recycles the heat of condensation of the distillate to the distilland.

Yet another object of the present invention is to provide a distillation process and apparatus which has a very low energy requirement.

It is also an object of the present invention to provide a distillation process and apparatus which can effectively utilize solar energy to meet most of its energy requirements.

Another object of the present invention is to provide a distillation process and apparatus which can utilize the energy released by combustion of fossil fuels or renewable biomass (e.g., wood) as a supplemental heat source or as a complete heat source.

Another object of the present invention is to provide a distillation process and apparatus which is particularly well suited for separating alcohol from an aqueous fermentation liquor.

A further object of the present invention is to provide a distillation process and apparatus which is compact and relatively portable, suitable for use on individual farms.

It is also an object of the present invention to provide a distillation process and apparatus which can effectively use waste process heat to meet at least part of its energy requirements.

SUMMARY OF THE INVENTION

These and other objects of the invention are achieved by providing a distillation process comprising the steps of providing a body of a liquid mixture to be distilled in a closed container, passing liquid vapors from said container to a vapor heating chamber, heating vapors in said vapor heating chamber, withdrawing heated vapors from said vapor heat chamber, compressing the withdrawn vapors, passing compressed vapors in heat exchange relation with said body of liquid mixture in said container, thereafter introducing compressed vapors into a reflux column disposed in said container in the interior of said body of liquid mixture to be distilled, collecting a less volatile condensate fraction from the bottom of said reflux column, withdrawing a more volatile vapor fraction from the top of said reflux column, passing said withdrawn vapor fraction in further heat exchange relation with said body of liquid mixture to be distilled, and collecting a more volatile condensate fraction.

In further refinements of the process of the invention, the objects are also achieved by passing the vapors withdrawn from the vapor heating chamber in heat exchange relation with steam produced by combustion of fossil fuels or wood to further heat the vapors prior to compressing them, by recirculating a portion of the more volatile condensate fraction back to the reflux column to promote refluxing in the column, or by recirculating a portion of the less volatile condensate fraction back to the distilland mixture to recover more volatile material present therein.

The objects of the invention are also achieved by providing a distillation apparatus comprising container means for a liquid mixture to be distilled, a vapor heating chamber, means communicating between said container means and said vapor heating chamber to permit free passage of liquid vapors from said container to said chamber, a reflux column disposed in the interior of said container means; first conduit means for withdrawing vapors from said vapor heating chamber, second conduit means communicating with said first conduit means for passing the withdrawn vapors in heat exchange relation with the liquid mixture to be distilled and then introducing said withdrawn vapors into said reflux column; compressor means associated with one of said first and second conduit means for maintaining a higher pressure in said reflux column than in said vapor heating chamber, means for collecting a less volatile condensate fraction from the bottom of said reflux column, third conduit means for withdrawing a more volatile vapor fraction from the top of said reflux column and passing said withdrawn vapor fraction in further heat exchange relation with said liquid mixture, and means for collecting a more volatile condensate fraction from said third conduit means.

In further refinements of the apparatus of the invention, the objects of the invention are also achieved by providing means for passing vapors withdrawn from the vapor heating chamber in heat exchange relation with steam produced by combustion of fossil fuels or wood to further heat the vapors prior to compressing them, by providing means for recirculating a portion of the more volatile condensate fraction back to the reflux column to promote refluxing in the column or by providing means for recirculating a portion of the less volatile condensate fraction back to the distilland liquid mixture to facilitate recovery of more volatile material present therein.

BRIEF DESCRIPTION OF THE DRAWING

Details of a preferred embodiment of the process and apparatus of the invention will be explained with reference to the accompanying drawing which is a schematic elevation of apparatus according to the invention suitable for carrying out the process of the invention.

DETAILED DESCRIPTION OF THE PREFERRED EMBODIMENT

The FIGURE shows a distillation apparatus generally designated by reference numeral 1 comprising a generally cylindrical container 2 defined by wall 3 for containing a body of liquid mixture 4 to be distilled. An inlet 5 is provided for admitting the liquid mixture into the container, and an outlet 6 is also provided to enable the liquid to be withdrawn from the container if necessary. The top of the container is defined by a partition 7 which also serves as the bottom of a vapor heating chamber 8 which is disposed above the liquid container. Chamber 8 is defined by a generally concical metal wall 9.

In the illustrated embodiment, chamber 8 is designed to be heated by solar energy. Accordingly, wall 9 is disposed at an angle of approximately 45 degrees in order to maximize the incidence of solar radiation thereon. Wall 9 is made of a heat conductive metal and preferably is painted black in order to maximize the absorption of solar energy. An opening 10 is provided through partition 7 through which vapors may pass from container 2 to chamber 8. If desired, the interior of the chamber wall may be provided with heat conductive metal fins 42 to assist in transferring energy to the vapors within the chamber.

A conduit 11 is provided for withdrawing vapors from the vapor heating chamber. The mouth 12 of conduit 11 is located near the peak or top of vapor heating chamber 8 so as to collect the hottest vapors. Conduit 11 extends downwardly through the interior of the vapor heating chamber along wall 9 and then exists from the distillation apparatus adjacent the bottom of vapor heating chamber 8. Such an arrangement of the conduit prevents the conduit from casting a shadow on the solar receiving surface of wall 9.

A heat exchanger 13 may be provided on conduit 11. About half way down the side of container 2, conduit 11 connects with conduit 14 which enters the device through container wall 3 and extends through the body of liquid 4 to a vertically oriented reflux column 15 and opens at 16 into the middle of the reflux column. Column 15 is vertically oriented and is located in the interior of container 2 near the center. A series of trays 17 are disposed inside reflux column 15 in order to promote refluxing the vapors in the column. The column may also be provided with any of the known forms of packing material 43 such as Raschig rings or Berl saddles. A small compressor or pump 18 is positioned on line 11 outside container 2. Conduit 11 is also provided with a vent line 19 and with a valve 20 for selectively closing off conduit 14 and opening vent line 19.

The bottom 21 of reflux column 15 is perforated or porous and communicates through the floor 22 of container 2 with a first condensate collecting tank 23 located underneath container 2. A body of condensed liquid 24 is shown in tank 23. An outlet 25 is provided so that condensed liquid can be withdrawn from collecting tank 23 as desired. A recycle line 26 leading from collecting tank 23 back to distilland container 2 is also provided to facilitate recirculation of condensate from collecting tank 23 back to the distilland liquid mixture. Valve 27 controls the flow of recycle liquid can be withdrawn from collecting tank 23 as desired.

A third conduit means 28 leads from an opening 29 at the top of reflux column 15 through the body of liquid in container 2 and opens at 20 through the floor 22 of container 2 into a second condensate collecting tank 31. Condensed liquid 32 which forms in tank 31 may be withdrawn as desired through outlet 33. Condensate from collecting tank 31 may also be recycled via recirculation line 34 back to reflux column 15 to promote refluxing in the column. A pump 35 and a valve 36 are provided on line 34 to initiate and regulate the flow of condensate back to column 15.

To permit the interior of container 2 to be inspected and/or cleaned, a sealable inspection port 37 is provided through wall 3 of container 2. The cover of inspection port 37 may be provided with handle grips 38 to facilitate its removal and replacement.

The entire device may be constructed of such size so as to be conveniently portable. The illustrated embodiment is designed to rest on a skid or pallet (not shown). A lifting hook 39 is located at the top of the apparatus to facilitate moving it from one location to another.

The entire apparatus is surrounded by a transparent shield 40 made of a material such as acrylic plastic or glass having a high coefficient of transmission for infrared radiation. Shield 40 is spaced approximately $\frac{1}{2}$ inch to $1\frac{1}{2}$ inches, preferably about 1 inch from the black outer walls of the apparatus and provides an insulating air space 41 to retard heat losses from the distillation apparatus to the surrounding atmosphere.

In operation of the device, inspection port 37 and outlet 6 are closed, and biomass fermentation liquor from, for example, fermentation of agricultural wastes such as spoiled grain, is introduced through inlet 5 until container 2 is nearly full. Inlet 5 is then closed and sealed. Valve 20 is adjusted to close off conduit 14 between compressor 18 and reflux column 15 and to open conduit 11 to the atmosphere through vent line 19.

Compressor 18 is then energized to evacuate heating chamber 8 to subatmospheric pressure. Preferably, the pressure in heating chamber 8 will be reduced to between about 0.2 and about 12 p.s.i.a. When the desired pressure has been achieved, valve 20 is again switched to close off vent line 19 and to connect compressor 18 to reflux column 15 via conduit 14. Since the pressure in vapor heating chamber 8 is less than the vapor pressure of liquid mixture 4 in container 2, liquid vapors pass from container 2 through opening 10 into the vapor heating chamber. As a result of solar radiation impinging on wall 9 of chamber 8, the vapors in the chamber are heated to a temperature between about 10 and about 60 degrees F. above the temperature of liquid mixture 4. For effective transfer of heat back to the distilland, the temperature of the vapors should be increased to at least 10 to 15 degrees F. above the temperature of the distilland mixture. Hot liquid vapors are withdrawn from the vapor heating chamber through opening 12 of conduit 11 and pass to compressor 18. Vapors leaving compressor 18 pass through conduit 14 in heat exchange relation with the liquid mixture 4. In the compressor, the pressure of the vapors is increased at least to above the vapor pressure of the less volatile component of the liquid mixture at the prevailing temperature at the inlet to the column 15 so that vapors of the less volatile component condense in the column while vapors of the more volatile component pass upwardly through the column and out the top. Pressures in the reflux column desirably will range between about 12 and about 20 p.s.i.a., preferably between about 14 and about 18 p.s.i.a. Condensation of the vapors is thereby induced. The pressure differential across compressor 18 is relatively small, and accordingly, the energy requirement of the compressor is very modest.

The heat released by the vapors upon condensation is transferred to the liquid mixture 4 as the vapors and initial condensate pass through conduit 14 to reflux column 15. In reflux column 15, vapors of the less volatile constituent of the liquid mixture, i.e., water, continue to condense and give off their heat. Alcohol vapors, which are more volatile than the water, are less likely to condense and pass upwardly to the top of the column. Refluxing from tray to tray in the column provides a good separation of the alcohol vapors and the water vapor. Condensed water collects at the bottom of reflux column 15 and passes through the perforated or porous bottom wall 21 into condensate collecting tank 23. If the condensate in collecting tank 23 is found to contain appreciable amounts of alcohol, it may be recycled to the body of distilland liquid 4 through recycle line 26 merely by opening valve 27. The pressure differential across the system will force the condensate through recirculation line 26 without the need for a pump.

Alcohol vapors are withdrawn through opening 29 at the top of reflux column 15 and pass through conduit 28 in further heat exchange relation with the liquid mixture 4. As the alcohol vapors pass through conduit 28, they continue to cool until they condense and give off more of their heat to the liquid mixture. Alcohol condensate passes through opening 30 at the end of conduit 28 into collecting tank 31. This condensate, which is designated by reference numeral 32, is about 160 proof and is suitable for use as an alcohol fuel. Condensate may be withdrawn as desired through outlet 33. To promote refluxing in column 15 in order to obtain better separation of the water and the alcohol, a portion of the condensate 32 from collecting tank 31 may be withdrawn through recirculation line 34 and introduced near the top of column 15.

The heat given off to the liquid mixture 4 by the vapors as they condense in conduit 14 and conduit 28 fosters further evaporation of the liquid mixture. Conduits 14 and 28 may be given a helical or serpentine configuration in order to provide a convoluted pathway for the heated and compressed vapors thereby to maximize the transfer of heat from the vapors to the liquid mixture. In steady state operation the temperature of the distilland may rise a few degrees to 10 or 15 degrees F. above ambient as a result of this heat transfer. If solar heating of the vapors is supplemented by a source of process heat, distilland temperatures may rise to 80 degrees F. or more above ambient.

An important aspect of the invention is the concept of vapor heating. The energy from solar radiation is not transferred directly to the body of liquid to be distilled, but instead is used to heat the vapors in vapor heating chamber 8 and is thereafter transferred to the liquid as the vapors are condensed in the interior of the distilland liquid mixture. Of course, some heat is supplied to the system by the compressor, but the amount is comparatively minor. The bulk of the heat energy in the system comes from the heating of the vapors by solar energy and/or a source of process heat. Vapor heating is an important concept and function because the temperature of the condensing vapors has to be at least 5 to 10 degrees above that of the liquid distilland to effect heat transfer from the condensing vapors to the distilland; also because it is more economical to use forms of energy other than that supplied by compression required for distillation and heat loss replacement. Very high thermal efficiencies are achieved because the energy of condensation is recycled to the distilland to promote further evaporation.

If desired, the vapors may be heated by means other than solar energy. For example, the compressor may be driven by an alcohol engine 44, and the hot exhaust gases from the engine may be passed through heat exchanger 13 in heat exchange relation with the vapors in order to provide supplemental heat energy to the vapors and conserve some of the exhaust heat which otherwise would be wasted. It is understood that other sources of process heat could also be used to heat the vapors either supplemental to or in place of solar heating. For example, steam produced in an external boiler (not shown) by burning fossil fuels such as coal or oil or by burning biomass such as wood chips etc., could be passed through heat exchanger 13 to heat the vapors as they pass through conduit 11. Electric energy could also be used to heat the vapors, but in most cases this would not be economically efficient. If the vapors are heated by a source of process heat rather than by solar radiation alone, then operating temperatures may range as high as 150 to 300 degrees F. and operating pressures may extend into the superatmospheric range to as much as 50 to 100 p.s.i.a.

The process and apparatus of the invention are especially suitable for use on individual farms. A device having the capacity to distill 100 to 200 or more gallons of alcohol per day can be manufactured comparatively economically and transported readily. Neither a great deal of technical expertise nor continuous attention are required for operation of the device. Agricultural products may be fermented substantially at their point of origin to produce alcohol which in turn can be consumed as fuel on the farm. This produces additional savings in energy otherwise required to transport the agricultural waste to remote fermentation sites and to haul fuel produced at remote locations to the farm for use thereon.

The foregoing embodiments have been described solely as examples of the invention and are not intended to be limiting. Since modifications of the disclosed embodiments, such as providing a plurality of interconnected fractionation columns in the container, may occur to persons skilled in the art, the scope of the invention is to be limited solely by the scope of the appended claims.

What is claimed is:

1. A distillation apparatus comprising container means for a liquid mixture to be distilled, a vapor heating chamber, means communicating between said container means and said vapor heating chamber to permit free passage of liquid vapors from said container to said chamber, a reflux column disposed in the interior of said container means; first conduit means for withdrawing vapors from said vapor heating chamber, second conduit means communicating with said first conduit means for passing the withdrawn vapors in heat exchange relation with the liquid mixture to be distilled and then introducing said withdrawn vapors into said reflux column; compressor means associated with one of said first and second conduit means for maintaining a higher pressure in said reflux column than in said vapor heating chamber, means for collecting a less volatile condensate fraction from the bottom of said reflux column, third conduit means for withdrawing a more volatile vapor fraction from the top of said reflux column and passing said withdrawn vapor fraction in further heat exchange relation with said liquid mixture, and means for collecting a more volatile condensate fraction from said third conduit means.

2. Apparatus according to claim 1 wherein said vapor heating chamber is heated by solar energy.

3. Apparatus according to claim 2, wherein said vapor heating chamber is constructed with heat conductive metal walls and provided with a black exterior surface to maximize absorption of solar energy.

4. Apparatus according to claim 2, wherein said vapor heating chamber has walls which are inclined at an angle of 45 degrees in order to increase the incidence of solar radiation thereon.

5. Apparatus according to claim 1, wherein said container means comprises a cylindrical container and said vapor heating chamber comprises a conical chamber disposed on top of said container means.

6. Apparatus according to claim 3, wherein said vapor heating chamber is provided with heat conducting metal fins extending from the chamber wall into the interior of the chamber.

7. Apparatus according to claim 1, wherein said reflux column is provided with a series of internal trays in order to increase the separation efficiency of the column.

8. Apparatus according to claim 1, wherein said reflux column is a packed column.

9. Apparatus according to claim 1, further comprising heat exchange means on said second conduit means providing a convoluted pathway for heated and compressed vapors in order to maximize the transfer of heat from said vapors to the body of liquid mixture to be distilled.

10. Apparatus according to claim 1, further comprising heat exchange means on said third conduit means providing a convoluted pathway for said volatile vapor fraction in order to maximize the transfer of heat from said fraction to the body of liquid mixture to be distilled.

11. Apparatus according to claim 1, further comprising a first collecting tank underneath said container means communicating with the bottom of said reflux column through a porous plate.

12. Apparatus according to claim 1, further comprising a second collecting tank underneath said container means into which said third conduit means leads.

13. Apparatus according to claim 1, wherein the apparatus is designed to be portable and provided with a lifting hook at the top thereof.

14. Apparatus according to claim 1, further comprising a closeable inspection port through the wall of said container means.

15. Apparatus according to claim 1, wherein said container means is provided with a transparent insulating shield for preventing loss of heat to the surrounding atmosphere.

16. Apparatus according to claim 1, wherein said first conduit means opens near the top of said vapor heating chamber and extends downwardly through the interior of said vapor heating chamber and exits adjacent the bottom of said vapor heating chamber.

17. Apparatus according to claim 1, further comprising means associated with said first conduit means for passing a source of process heat in heat exchange relation with vapors withdrawn from said vapor heating chamber.

18. Apparatus according to claim 17, wherein exhaust gases from a power source used to drive said compressor means are passed in heat exchange relation with the vapors from the vapor heating chamber.

19. Apparatus according to claim 1, further comprising means for recirculating a portion of said more volatile condensate fraction back to said reflux column.

20. Apparatus according to claim 1, further comprising means for recirculating a portion of said less volatile condensate fraction back to said container means.

* * * * *